(12) United States Patent
Pozzato

(10) Patent No.: US 6,458,122 B1
(45) Date of Patent: Oct. 1, 2002

(54) RADIOFREQUENCY ELECTROSURGICAL GENERATOR WITH CURRENT CONTROL

(75) Inventor: Gianantonio Pozzato, Vicenza (IT)

(73) Assignee: Telea Electronic Engineering SRL, Vicenza (IT)

( * ) Notice: Subject to any disclaimer, the term of this patent is extended or adjusted under 35 U.S.C. 154(b) by 0 days.

(21) Appl. No.: 09/719,783

(22) PCT Filed: Jun. 18, 1998

(86) PCT No.: PCT/EP98/03735

§ 371 (c)(1),
(2), (4) Date: Dec. 18, 2000

(87) PCT Pub. No.: WO99/65411

PCT Pub. Date: Dec. 23, 1999

(51) Int. Cl.[7] .............................................. A61B 18/00
(52) U.S. Cl. .......................................... 606/37; 606/39
(58) Field of Search .............................. 606/37, 38, 39, 606/40

(56) References Cited

U.S. PATENT DOCUMENTS

| | | | | |
|---|---|---|---|---|
| 3,730,188 A | * | 5/1973 | Ellman | 606/37 |
| 4,429,694 A | | 2/1984 | McGreevy | |
| 4,590,934 A | | 5/1986 | Malis et al. | |
| 5,954,686 A | * | 9/1999 | Garito et al. | 604/37 |
| 6,142,992 A | * | 11/2000 | Cheng et al. | 606/38 |

FOREIGN PATENT DOCUMENTS

FR 2508792 1/1983

OTHER PUBLICATIONS

WO 98/07378, Scott A. Miller, Improved Electrosurgical Generator, Feb. 26, 1998.

* cited by examiner

Primary Examiner—Gerald A. Michalsky
(74) Attorney, Agent, or Firm—Dykema Gossett PLLC

(57) ABSTRACT

The invention realizes a radio knife powered by an electronic circuit that operates with high-frequency current wherein said circuit comprises: a rectifier circuit (20) fed by the mains voltage that supplies rectified pulsating voltage (201) to a radiofrequency circuit (30); a radiofrequency circuit (30) capable of emitting an output current signal (301) with a constant frequency in the scale of the MHz, powering the radio knife by means of a radiofrequency transformer (40). Said radiofrequency circuit (30) is obtained by piloting a MOSFET (305) through a pilot circuit (306) comprising a quartz-operated oscillator whose oscillation frequency amounts to at least twice the usual operating frequency of the MOSFET. The pilot circuit (306) is controlled by microprocessor current control circuit (310) that takes a signal proportional to the current from a current sensor (308) positioned after the MOSFET (305) and is such as to maintain the radiofrequency circuit current limited to a value compatible with the power that can be dissipated by the MOSFET independently of any variation in the circuit load impedance.

11 Claims, 1 Drawing Sheet

RADIOFREQUENCY ELECTROSURGICAL GENERATOR WITH CURRENT CONTROL

The invention concerns a radio knife operating with high-frequency currents of approximately 4 MHz.

It is known that a radio knife is defined as an instrument used in surgery to cut tissues, comprising a generator of high-frequency current with intensity equal to a few hundred milliamperes provided with two electrodes, one of which is called plate, while the other, called handpiece, is active and has the shape of a needle, a small sphere or a bevelled blade. The patient on whom the radio knife must be used rests his/her body on the plate, while the radio knife is used for the operation. The cutting of the tissues is proportional to the intensity of the current passing between the electrodes and compared to the traditional knife with steel cutting blade this instrument offers the advantage of an almost complete hemostasis due to the coagulating action on the small vasa of the tissues and of a limited destruction of cells.

It is also known that the quantity of necrotized tissues produced during the cutting depends on the frequency of the generator current and tends to decrease as said frequency increases, said frequency being generally fixed in a few hundred kHz. A further increase in said frequency makes it necessary to use particular electronic components, such as vacuum tubes, makes the produced frequency unstable and requires high voltages in order to guarantee a constant cutting current. Furthermore, the use of vacuum tubes to generate high frequencies may prevent the necessary insulation of the circuit in which the cutting current flows from the surrounding environment, which does not ensure enough safety.

US 4,590,934 discloses a bipolar cutter/coagulator at the forceps of which there is waveform with the frequency of 1 MHz when the device operates as cutter. The waveform frequency varies between limits of 1 MHz plus or minus 4% when the device operates as coagulator.

The aim of the present invention is the implementation of a radio knife preferably operating with a 4 MHz frequency, so that no necrotic effect is produced on the cells adjacent to the cut according to the operating procedure described below.

Another aim of the invention is the implementation of a radio knife with standard solid components, which make it possible to employ limited voltages for the operation of the device and guarantee highly stable frequencies and the possibility of use for any type of operation, since the power delivered is independent of the load impedance.

The radio knife object of the invention should also ensure high safety levels and a cut with no necrotic effects on the adjacent cells, so that it is possible to use the equipment also on extremely delicate tissues (for example, the brain) and to use the local anaesthesia instead of the general anaesthesia, with obvious advantages for the recovery of the patient.

All the goals mentioned above and others that will be better highlighted below have been achieved through the implementation of a high-frequency radio knife that, according to the main claim, comprises a handpiece for the cut and a plate closing an electronic circuit, said circuit comprising:
  a rectifier circuit fed by the mains voltage that supplies rectified pulsating voltage to a radiofrequency circuit;
  a radiofrequency circuit capable of emitting an output current signal with a constant frequency of a few MHz, powering the radio knife by means of a radiofrequency transformer, and wherein said radio knife is characterized in that the radiofrequency circuit is obtained by piloting a MOSFET through a pilot circuit comprising a quartz-operated oscillator whose oscillation frequency amounts to at least twice the usual operating frequency of the MOSFET, said pilot circuit being controlled by a microprocessor current control circuit that takes a signal proportional to the current from a current sensor positioned after the MOSFET and is such as to maintain the radiofrequency circuit current limited to a value compatible with the power that can be dissipated by the MOSFET independently of any variation in the circuit load impedance, said impedance being constituted by the MOSFET stray capacitance, the radiofrequency transformer inductance and the impedance of the patient's body part positioned between the radio knife and the circuit closing plate.

To advantage, according to the invention a 4 MHz frequency on the handpiece is used, with a substantially constant current independently of the load variation, which ensures a cut without necrosis; in fact, by properly proportioning the power the instantaneous evaporation of the intracellular liquids is obtained, thus taking heat from the cut area and preventing the spreading of said heat to the adjacent cells, which protects them against any damage.

It has been observed that 4 MHz is the optimal frequency, in fact a further increase in frequency would be detrimental, since the excessive reduction in the evaporation time would require a power increase that produces unwanted, damaging effects on the adjacent cell layers. It can therefore be concluded that the 4 MHz frequency represents the optimal operating value for a radio knife that does not produce any necrotic effect. This underlines also the importance of the stability of the operation frequency over time, independently of any variation in the power delivered and the load impedance that is constituted, as far as the current generator is concerned, by the tissues to be cut and can vary, according to the kind of operation, from a few dozen ohms to the kohm.

According to the application proposed by the invention, this result is achieved, as already explained, through the use—for the high-frequency oscillator—of quartz-operated standard MOSFET adjusted by a current control device. The use of solid components to obtain high-frequency currents has considerable advantages compared to the use of vacuum tubes, due to the greater reliability of the former, to the lower voltages necessary for their operation and to their greater stability. However, there is a difficulty represented by the fact that the MOSFET operating with high frequency (radiofrequency MOSFET) can seldom support voltages exceeding 100 V, which are absolutely unsuitable for the application in question; on the other hand, the operating frequency of the MOSFET that are capable of supporting the 700–800 V required for the generator of a radio knife usually does not exceed 1 MHz.

The solution proposing the use of the circuit object of the invention makes it possible to employ standard MOSFET to obtain the high-frequency oscillator, though obtaining a 4 MHz current generator with voltages of approximately 700 V.

A further advantage is represented by the fact that the generator frequency is kept constant by means of a quartz-operated oscillator, while the current, in case of decrease in the load value, is automatically limited, in such a way as to guarantee the required power independently of the load impedance itself, that is, of the type of tissue and of operation. This is achieved by producing the required frequency with a quartz-operated oscillator that pilots the MOSFET operating in class C, since the resonant load is the result of the combination of the radiofrequency transformer inductance and of the stray capacitance of the MOSFET itself.

The current limitation is obtained on the MOSFET circuit through a hard-wired logic with quick comparators controlled by a microprocessor.

The solution object of the invention is also characterized by the fact that the current circuit is completely and galvanically insulated through the radiofrequency transformer (that is, the load is floating), in such a way as to make the equipment suitable for being operated together with other equipment (since it respects the current dispersion limits), thus making it impossible to operate the cutting current if not through the volume included between the plate and the handpiece, with evident advantages for the operators' safety.

Further characteristics and details of the invention will be better highlighted in the description of a practical application among many of the invention in question, illustrated in the enclosed drawings, wherein.

Figure 1:
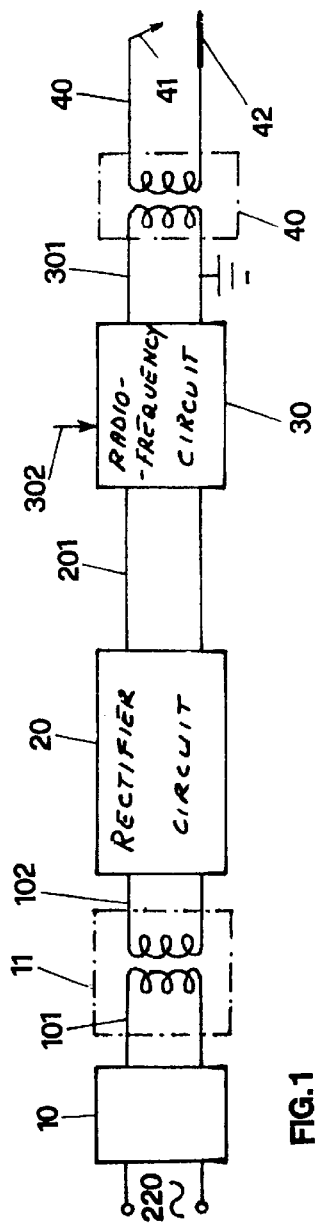
FIG. 1 is a block diagram of the radio knife object of the invention.
Figure 2:
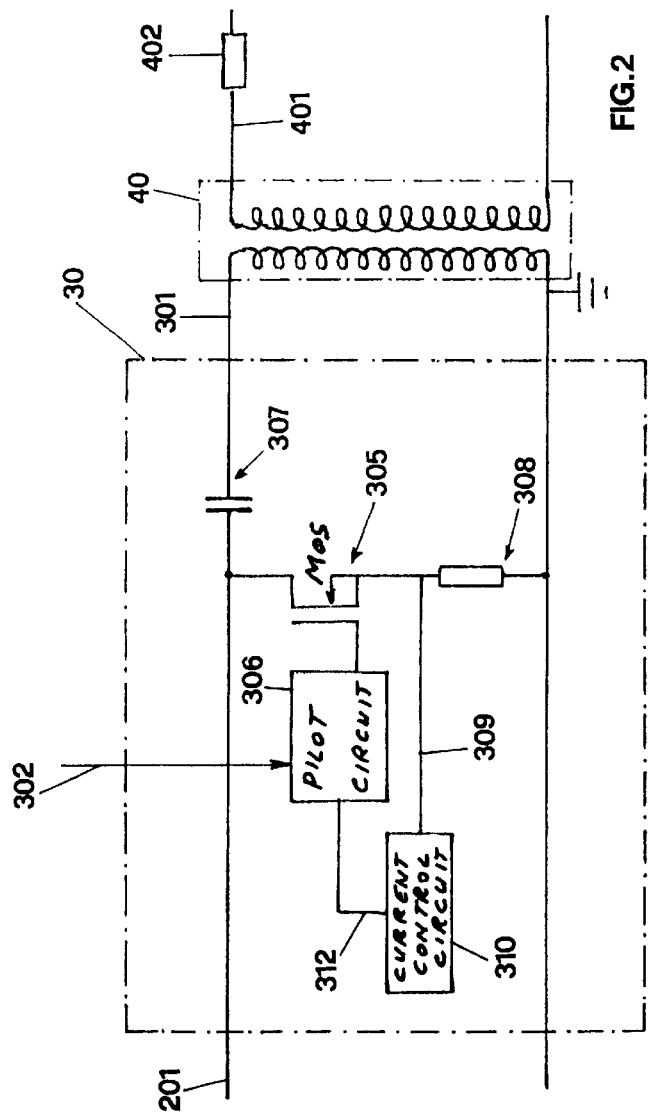
FIG. 2 shows the radiofrequency circuit relevant to the radio knife of FIG. 1 in detail.

With reference to the above mentioned figures, it can be observed that the radio knife circuit is fed by the 220 V mains voltage and is provided with an input filter 11 ensuring protection against possible radiofrequency disturbances present in the mains. The circuit comprises also a transformer indicated by 11 with an input voltage amounting, for example, to 220 V and an output voltage ranging approximately from 100 to 160 V. This voltage enters the high-frequency rectifier circuit 20, which is a normal diode rectifier circuit with two half waves that transforms alternated current into pulsating current and then rectifies it, so that the continuous output voltage that constitutes the power supply of the radiofrequency circuit 30 is rather high, for example 220 V. Said radiofrequency circuit is better represented in FIG. 2.

It comprises an electronic component MOSFET 305 piloted by a pilot circuit 306, which in turn is operated by a current control device 310. More precisely, the circuit 30 consists of a MOSFET 305 that works as a switch and interrupts the direct current coming from 201 with a frequency imposed by the pilot circuit 306. The frequency of the pilot circuit 306 is kept constant by means of the quartz-operated circuit and therefore the MOSFET 305 is operated through a signal having the quartz oscillation frequency, which in the case illustrated in the example is equal to 4 MHz. When the MOSFET closes, it interrupts the current on the branch 301 and when it opens it allows the passage of the current to the branch 301. The duration of the passage of current depends on the power adjustment in 302, wherein the power regulator 302 is an external device that makes it possible to choose the amplitude of the output wave, so that the power of the radio knife can be set according to the type of operation to be carried out.

The output of the radiofrequency circuit is a pulse current wave 301 at the frequency of 4 MHz, whose amplitude is controlled by the power regulator 302. The current signal 301 passes through the radiofrequency transformer 40 and is transformed into a practically sinusoidal 4 MHz signal 401 with voltages ranging from approximately 300 V to approximately 700 V and with currents of 700–800 mA.

It can be observed that, once the power regulator has been set, the current of signal 401 is substantially independent of the impedance present between the knife 41 and the plate 42. The MOSFET 305, through the condenser 307, the primary winding of the transformer 40 and the intrinsic stray capacitances of the MOSFET itself operates so that at the end 401 the radio knife practically works with a pulse current combined with a practically sinusoidal voltage. This means that the radio knife operates as if closed on a resonant load with a single resonance frequency.

The current 401 is maintained at a substantially constant value independently of the impedance by means of a current control device coming from a current sensor 308 positioned after the MOSFET 305. The voltage signal 309, coming from the current sensor 308 controls the current control device 310 that, among its other functions, limits the maximum current 401 by means of quick comparators controlled by a microprocessor, acting with the signal 312 on the MOSFET pilot circuit.

Since in case of low impedance the current would reach very high values, the circuit is provided with a current limiter constituted by the inductance 402 that limits the current supplied to the handpiece and prevents the circuit from exceeding the maximum current value permissible.

What is claimed is:

1. A radio knife comprising a cutting handpiece and a plate powered by an electronic circuit comprising:
   a rectifier circuit fed by mains voltage that supplies rectified pulsating voltage to a radiofrequency circuit;
   said radiofrequency circuit suited to issue an output current signal with a constant frequency feeding the radio knife by means of a radiofrequency transformer,
   said radiofrequency circuit having a MOSFET piloted by a pilot to a circuit comprising a quartz-operated oscillator,
   said pilot circuit being connected to a microprocessor current control circuit which takes a signal from a current sensor present downstream in respect to said MOSFET and suited to maintain the current of said radiofrequency circuit limited to a value compatible with the power dissipatable by said MOSFET independently of any variation in the circuit load impedance,
   said impedance comprising also a patient's body part impedance positioned between the radio knife and the circuit closing plate,
   wherein said pilot circuit feeds said MOSFET with a frequency substantially of 4 MHz, said frequency being equal to the frequency of the current present in said handpiece.

2. The radio knife according to claim 1, wherein the tension of the handpiece remains substantially sinusoidal, a condenser being present upstream the radiofrequency transformer.

3. The radio knife according to claim 1, wherein downstream the radiofrequency transformer is present an impedance suitable to limit the current of the handpiece to avoid to overcome the maximum value of the current for said handpiece.

4. The radio knife according to claim 1, wherein the current of the handpiece is maintained substantially constant when the global impedance of the load is varying, by a current control operated by a current sensor.

5. The radio knife according to claim 1, wherein the MOSFET used in said radiofrequency circuit is a standard MOSFET having a high level of output power, said MOSFET having an input of a quartz operated oscillator with oscillations at 4 MHz.

6. A radio knife comprising a cutting handpiece and a plate powered by an electronic circuit comprising:
   a rectifier circuit fed by mains voltage that supplies rectified pulsating voltage to a radiofrequency circuit;
   said radiofrequency circuit suited to issue an output current signal with a constant frequency feeding the radio knife by means of a radiofrequency transformer, said radiofrequency circuit having a MOSFET piloted by a pilot to a circuit comprising a quartz-operated oscillator, said pilot circuit being connected to a microprocessor current control circuit which takes a signal from a current sensor present downstream in respect to said MOSFET and suited to maintain the current of said radiofrequency circuit limited to a value compatible with the power dissipatable by said MOSFET independently of any variation in the circuit load impedance, said impedance comprising also a patient's body part impedance positioned between the radio knife and the circuit closing plate, wherein said pilot circuit feeds said MOSFET with a frequency substantially of 4 MHz, said frequency being equal to the frequency of the current present in said handpiece, and said electronic circuit generates power greater than 100 W.

7. The radio knife according to claim 6, wherein the tension of the handpiece remains substantially sinusoidal, a condenser being present upstream the radiofrequency transformer.

8. The radio knife according to claim 6, wherein downstream the radiofrequency transformer is present an impedance suitable to limit the current of the handpiece to avoid to overcome the maximum value of the current for said handpiece.

9. The radio knife according to claim 6, wherein the current of the handpiece is maintained substantially constant when the global impedance of the load is varying, by a current control operated by a current sensor.

10. The radio knife according to claim 6, wherein the MOSFET used in said radiofrequency circuit is a standard MOSFET having a high level of output power, said MOSFET having an input of a quartz operated oscillator with oscillations at 4 MHz.

11. A radio knife having a radio frequency (RF) power input and being carried by a cutting hand piece for performing surgery on a body part of a patient representing a variable load impedance and a conductive plate for contacting the patient and closing an electronic circuit comprising:

a rectifier circuit for producing a rectified pulsating voltage;

an RF circuit coupled to the rectifier having an output for producing RF power sufficient to effect hemostasis at a selected voltage and current level and at a substantially constant frequency selected to produce said hemostasis without producing necrosis;

an RF transformer coupled between the RF output and the power input of the knife for raising the voltage of the RF power output to said selected level;

the RF circuit including a MOSFET current source having an output circuit coupled to the output of the RF circuit and an input, and an oscillator coupled to the input for modulating the MOSFET to the selected frequency, said MOSFET for producing the selected output current;

a current sensor located in the output circuit of the MOSFET for producing an output indicative of the current in the MOSFET output circuit; and a microprocessor control responsively coupled to the current sensor and operatively coupled to the oscillator for producing a current limiting signal for controlling the oscillator gating the MOSFET, such that the selected current produced in the output circuit of said MOSFET is limited to a value compatible with the MOSFET and which selected current is independent of variations in the load impedance.

\* \* \* \* \*